(12) United States Patent
Tan et al.

(10) Patent No.: US 11,103,585 B2
(45) Date of Patent: Aug. 31, 2021

(54) USE OF A POLYANIONIC COMPOSITION

(71) Applicant: Austrianova Singapore Pte Ltd., Singapore (SG)

(72) Inventors: Wee Jin Tan, Singapore (SG); Walter H. Gunzburg, Singapore (SG); John A. Dangerfield, Singapore (SG)

(73) Assignee: Austrianova Singapore Pte Ltd., Singapore (SG)

( * ) Notice: Subject to any disclaimer, the term of this patent is extended or adjusted under 35 U.S.C. 154(b) by 36 days.

(21) Appl. No.: 16/131,639

(22) Filed: Sep. 14, 2018

(65) Prior Publication Data
US 2019/0015514 A1     Jan. 17, 2019

Related U.S. Application Data

(63) Continuation of application No. 15/309,839, filed as application No. PCT/SG2015/050102 on May 8, 2015, now abandoned.

(30) Foreign Application Priority Data

May 9, 2014    (GB) ...................................... 1408233

(51) Int. Cl.
| | | |
|---|---|---|
| *A61K 47/36* | (2006.01) | |
| *C08L 5/00* | (2006.01) | |
| *C08L 5/02* | (2006.01) | |
| *C08L 1/16* | (2006.01) | |
| *C12N 5/00* | (2006.01) | |
| *A61K 9/48* | (2006.01) | |
| *A61K 35/22* | (2015.01) | |
| *C08L 39/00* | (2006.01) | |

(52) U.S. Cl.
CPC ............ *A61K 47/36* (2013.01); *A61K 9/4816* (2013.01); *A61K 9/4866* (2013.01); *A61K 35/22* (2013.01); *C08L 1/16* (2013.01); *C08L 5/00* (2013.01); *C08L 5/02* (2013.01); *C08L 39/00* (2013.01); *C12N 5/0012* (2013.01); *C08L 2203/02* (2013.01); *C08L 2205/03* (2013.01); *C12N 2533/30* (2013.01); *C12N 2533/70* (2013.01); *C12N 2533/78* (2013.01)

(58) Field of Classification Search
CPC ...... A61K 47/36; A61K 9/4816; A61K 9/486; A61K 35/22; C08L 39/00; C08L 1/16; C08L 5/00; C08L 5/02; C08L 2203/02; C08L 2205/03; C12N 5/0012; C12N 2533/30; C12N 2533/70; C12N 2533/78

See application file for complete search history.

(56) References Cited

U.S. PATENT DOCUMENTS

| | | |
|---|---|---|
| 4,407,957 A | 10/1983 | Lim |
| 5,531,735 A | 7/1996 | Thompson |
| 5,929,050 A | 7/1999 | Petito |
| 2006/0148074 A1 | 7/2006 | Gorfien et al. |

FOREIGN PATENT DOCUMENTS

| | | |
|---|---|---|
| EP | 2172264 A1 | 4/2010 |
| GB | 2094750 A | 9/1982 |
| WO | 1997/01357 A1 | 1/1997 |
| WO | 199735994 A2 | 10/1997 |
| WO | 1998027966 A2 | 7/1998 |
| WO | 2004047848 A1 | 6/2004 |
| WO | 2006095021 A1 | 9/2006 |
| WO | 2012101167 A1 | 8/2012 |
| WO | 2014185851 A1 | 11/2014 |
| WO | 2015000972 A1 | 1/2015 |

OTHER PUBLICATIONS

Esser-Kahn et al., 'Triggered release from polymer capsules', Macromolecules, 2011, vol. 44, pp. 5539-5553.
Desna Yes, S. et al., 'Polymeric biomaterials with engineered degradation', Journal of Polymer Science, 2013, vol. 51, pp. 3531-3566.
International Search Report issued from corresponding PCT/SG2015/050102, dated Jun. 22, 2015.
International Preliminary Report on Patentability issued in corresponding International Application No. PCT/SG2015/050102, dated Nov. 15, 2016.
Bioencapsulation of Living Cells for Diverse Medical Applications, E-Book. Editors: Brandtner EM, Dangerfield JA. Bentham Science Publishers; 2013, pp. i-184.
Lohr M, et al., Cell therapy using microencapsulated 293 cells transfected with a gene construct expressing CYP2B1, an ifosfamide converting enzyme, instilled intra-arterially in patients with advanced-stage pancreatic carcinoma: a phase I/II study, Journal of Molecular Medicine, 1999; 77(4):393-398.
Lohr M, et al., Microencapsulated cell-mediated treatment of inoperable pancreatic carcinoma, Lancet, 2001; 357(9268):1591-1592.
Lohr M, et al., Safety, feasibility and clinical benefit of localized chemotherapy using microencapsulated cells for inoperable pancreatic carcinoma in a phase I/II trial, Cancer Therapy, 2003; 1:121-131.
Hauser O, et al., Encapsulated, genetically modified cells producing in vivo therapeutics, Current Opinion in Molecular Therapeutics, 2004; 6(4):412-420.
Schaffellner S, et al., Porcine Islet Cells Microencapsulated in Sodium Cellulose Sulfate, Transplantation Proceedings, 2005; 37(1):248-252.

(Continued)

*Primary Examiner* — Matthew P Coughlin
*Assistant Examiner* — Thurman Wheeler
(74) *Attorney, Agent, or Firm* — Banner & Witcoff, Ltd.

(57) ABSTRACT

Disclosed herein is a use of a composition, comprising a non-toxic polyanionic material or a salt thereof to dissociate a polymeric membrane. In addition, a method of dissociating a polymeric membrane is also presented, the method comprising the steps of providing a polymeric membrane; and dissociating the polymeric membrane by adding a composition comprising a non-toxic polyanionic material to the polymeric membrane.

7 Claims, 3 Drawing Sheets

(56) References Cited

OTHER PUBLICATIONS

Stadlbauer V, et al., Morphological and functional characterization of a pancreatic beta-cell line microencapsulated in sodium cellulose sulfate/poly(diallyldimethylammonium chloride), Xenotransplantation, 2006; 13(4):337-344.

Pelegrin M, et al., Immunotherapy of a Viral Disease by in Vivo Production of Therapeutic Monoclonal Antibodies, Human gene therapy, 2000; 11(10):1407-1415.

Salmons B, et al., GMP Production of an Encapsulated Cell Therapy Product: Issues and Considerations, BioProcessing, 2007; 6(2):37-44.

Dangerfield JA, et al., The Diversity of Uses for Cellulose Sulfate Encapsulation., Chapter 3 in E-Book: Brandtner EM and Dangerfield, J.A., Eds. Bioencapsulation of Living Cells for Diverse Medical Applications, Bentham Science Publishers; 2013, pp. 70-92.

Gunzburg WH, Salmons B., Stem cell therapies: On track but suffer setback, Current opinion in Molecular Therapeutics, 2009; 11(4):360-363.

Bornens, M. et al., Isolation of Nuclear Envelopes with Polyanions, The Journal of Cell Biology,1978; vol. 76, pp. 191-206.

Dautzenberg, H. et al., Encapsulation by polyelectrolyte complex formation—a way to make hepatocyte cultures safe, efficient and on-line available, Immobilized Cells: Basics and Applications, 1996, pp. 181-188.

Jan. 7, 2015—(GB) Search Report—Appl No. 1508233.3.

Jul. 7, 2017—(US) Restriction Requirement—U.S. Appl. No. 15/309,839.

Dec. 1, 2017—U.S. Non-Final Office Action—U.S. Appl. No. 15/309,839.

Jun. 15. 2018—U.S. Final Office Action—U.S. Appl. No. 15/309,839.

Jan. 3, 2019—(TW) Office Action—Appl No. 104114899—Eng. Trans.

Jun. 3, 2019—(TW) Office Action—Appl No. 104114899—Eng. Trans.

Mar. 1, 2020—(TW) Certificate of Grant—Appl No. 104114899.

Oct. 16, 2017—(EP) Extended European Search Report—Appl No. 15789170.6.

Sep. 19, 2018—(EP) Office Action—Appl No. 15789170.6.

Feb. 24, 2020—(EP) Certificate of Grant—Appl No. 15789170.6.

Menvielle et al. "Dual Role of Dextran Sulfate 5000 Da as Anti-Apoptotic and Pro-Autophagy Agent" Mol. Biotechnol., Jun. 2013; 54(2):711-20.

USE OF A POLYANIONIC COMPOSITION

RELATED APPLICATION DATA

This application is a continuation application which claims priority to U.S. patent application Ser. No. 15/309,839, filed Nov. 9, 2016, which is a National Stage Application under 35 U.S.C. 371 of co-pending PCT application PCT/SG2015/050102 designating the United States and filed May 8, 2015; which claims the benefit of GB application number 1408233.3 and filed May 9, 2014 each of which is hereby incorporated by reference in its entirety.

TECHNICAL FIELD

The present invention relates to the use of a polyanionic composition to dissociate a polymeric membrane and a method of doing the same.

BACKGROUND

The listing or discussion of an apparently prior-published document in this specification should not necessarily be taken as an acknowledgement that the document is part of the state of the art or is common general knowledge.

Encapsulation is the process of forming a continuous coating around an inner matrix. The inner matrix is wholly contained within a capsule wall as a core of encapsulated material. Encapsulation must be distinguished from "immobilisation" which refers to the trapping of material within or throughout a matrix. In contrast to encapsulation, this is a random process resulting in an undefined particle size where a percentage of immobilised elements are exposed at the surface. In certain cases this may cause immunogenicity if implanted into the body. Encapsulation helps to separate a core material from its environment, thereby improving its stability, extending the core's shelf life and, in the case of implantation for medical uses, prevents capsules from being immunogenic. The structure formed by the encapsulation agent around the core substance is known as a "wall" or a "wall system". Properties of the "wall system" are designed to protect the core and, potentially, to release it under specific conditions while allowing small molecules to pass through the "wall" or "wall system". In addition, the "wall" or "wall system" may also be used in forms other than capsules. For example, the wall may act as a barrier confining the movement of one or more substances while allowing small molecules to pass through the "wall" or "wall system". The wall may be removed under specific conditions, allowing the one or more substances to move freely.

Various polymers can be used to generate capsules for the encapsulation of living cells. Some examples are alginate, collagen, gelatin, agarose, chitosan and cellulose sulfate (1). The most commonly used materials are alginates, which are natural anionic polysaccharides made up by D-mannuronic and L-guluronic acid residues joined linearly by 1-4 glycosidic linkages.

Cellulose Sulfate Microcapsules

An alternative encapsulation technology to alginate involves the forming of polyelectrolyte complex capsules by oppositely charged polyions. A particularly effective polyelectrolyte complex capsule is a capsule formed from sodium cellulose sulfate (NaCS or SCS) and poly[diallyl (dimethyl)-ammoniumchloride] (pDADMAC). The SCS/pDADMAC capsule is formed by dropping a solution of polyanionic SCS into a solution of polycationic pDADMAC. Advantageously, small substances such as nutrients and waste products can easily pass through the SCS/pDADMAC capsule pores while the pores block the exit/entrance of larger substances such as cells. The SCS/pDADMAC capsule is also biocompatible with cells and is non-immunogenic when implanted into the body. In addition, the long term survival (i.e. viability) of cells has been documented for many cell types which were encapsulated using the SCS/pDADMAC capsule system. Further, these capsules together with a cryopreservative agent can be frozen at minus 20° C., minus 80° C. or even in the vapour phase of liquid nitrogen without any damage at all to the SCS/pDADMAC capsule structure or its integrity. Moreover, cells that have been encapsulated using the SCS/pDADMAC capsules show excellent cell viability over long periods of time (up to at least 5 years). Accordingly, the SCS/pDADMAC capsules provide a useful technology for the easy storage and transport of encapsulated cells.

The SCS/pDADMAC capsules have been optimised for, and successfully used, in the clinic. For example, the SCS/pDADMAC capsules have been used in the field of tumour therapy where the encapsulated living cells produce a therapeutic enzyme to convey a chemotherapeutic agent to a tumour. Patients with non-resectable pancreatic cancer have been treated in such as way in clinical trials and the treatment was shown to be safe and efficacious (2-4). It has also been shown that the SCS/pDADMAC capsules can release many different kinds of biomolecules inside the body at physiologically effective doses (5-8). The biomolecules can pass through the capsule pores and include therapeutic antibodies, cytokines and insulin. Large scale pharmaceutical grade (GMP) manufacturing has also been established using the SCS/pDADMAC capsule technology (9). More recently, the technology has been shown to be useful for encapsulating sensitive types of cells (e.g. stem cells) and for the manufacturing of stem cells for therapeutic applications (10, 11). In addition, the SCS/pDADMAC capsule technology has also been shown to be useful for food, animal feed and neutraceutical applications. For example, the SCS/pDADMAC capsule technology can be used to encapsulate probiotic bacteria and protect the bacteria from stomach acid.

In summary, SCS/pDADMAC capsules can be described as a means to protect, isolate, store and transport a range of substances including any kind of living cell. Using eukaryotic cells, the uses are primarily in healthcare, biotechnology, veterinary and research (10). Using prokaryotic cells, the uses are primarily in probiotics, cosmetics, farming, agriculture and in environmental applications.

As well as protecting, isolating, storing and transporting cells, it would be desirable for an encapsulating technology system that can release the substances stored therein without denaturing said substance if required. For some applications in biotechnology and biomedicine, having the ability to release encapsulated cells is indispensable as, said cells need to be free (non-encapsulated) for downstream processing. Therefore, the concept of dissociating or fragmenting away the capsule material using a cell-friendly process, in the laboratory and/or in the body, would allow completely new applications for encapsulant technologies. Accordingly, there is a need for a composition capable of dissociating capsule materials in an environmentally- and cell-friendly manner.

SUMMARY OF INVENTION

In a first aspect of the invention, there is disclosed a use of a composition comprising a non-toxic polyanionic material or a salt thereof to dissociate a polymeric membrane. In certain embodiments, the non-toxic polyanionic material is a polysaccharide sulfate, a poly(sodium styrene sulfonate) or a polyacrylic acid or a salt thereof, provided that the polysaccharide sulfate is not a glycosoaminoglycan.

In embodiments of the invention, the polymeric membrane is in the form of a capsule that encapsulates a substance or in the form of a barrier that blocks free movement of a substance.

In further embodiments of the invention, the polymeric membrane may comprise sodium cellulose sulfate and polydiallyldimethylammonium chloride (pDADMAC).

In still further embodiments of the invention, the non-toxic polyanionic material may be a polysaccharide sulfate, a poly(sodium styrene sulfonate) or a polyacrylic acid or a salt thereof or, more particularly, the non-toxic polyanionic material is a polysaccharide sulfate, a poly(sodium styrene sulfonate) or a polyacrylic acid or a salt thereof, provided that the polysaccharide sulfate is not a glycosoaminoglycan. For example, the polyanionic material or a salt thereof may have a number average molecular weight of from 4,000 to 20,000 Daltons (e.g. a number average molecular weight of from 4,500 to 15,000, such as from 5,000 to 10,000, e.g. 5,000).

In embodiments of the invention, wherein a substance is mentioned, the substance may be selected from one or more of the group consisting of cells, proteins, biocompatible particles, and chemical compounds. For example, the substance is a plurality of cells.

In certain embodiments, the polyanionic material or salt thereof is a polysaccharide sulfate, optionally wherein each saccharide unit of the polysaccharide sulfate contains from 1 to 3 sulfate groups.

In certain embodiments, the polysaccharide sulfate or salt thereof is a carbohydrate sulfate or salt thereof, a glucosoaminoglycan sulfate or salt thereof or combinations thereof. In particular embodiments, the polysaccharide sulfate or salt thereof is a carbohydrate sulfate or salt thereof, provided that the carbohydrate sulfate is not a glucosoaminoglycan sulfate.

For example, the carbohydrate sulfate is one or more of the group consisting of dextran sulfate and cellulose sulfate with a number average molecular weight of from 4,000 to 20,000 Daltons and salts thereof (e.g. the carbohydrate sulfate is dextran sulfate or a salt thereof, such as dextran sulfate sodium salt).

For example, the glucosoaminoglycan sulfate is selected from the group consisting of heparin, heparan sulfate, chondroitin sulfate, dermatan sulfate and salts thereof.

In certain embodiments, the composition is an anticlumping agent comprising dextran sulfate.

In further embodiments, the composition may contain the polysaccharide sulfate in a concentration of from 0.1 mg/mL to 100 mg/mL (e.g. a concentration of from 1 mg/mL to 20 mg/mL).

In a second aspect of the invention, there is disclosed a method of dissociating a polymeric membrane, the method comprising the steps of:

(a) providing a polymeric membrane; and
(b) dissociating the polymeric membrane by adding a composition comprising a non-toxic polyanionic material to the polymeric membrane. In certain embodiments, the non-toxic polyanionic material is a polysaccharide sulfate, a poly(sodium styrene sulfonate) or a polyacrylic acid or a salt thereof, provided that the polysaccharide sulfate is not a glycosoaminoglycan.

In embodiments of the invention, the polymeric membrane may be in the form of a capsule that encapsulates a substance or in the form of a barrier that blocks free movement of a substance.

In further embodiments, the polymeric membrane comprises sodium cellulose sulfate and polydiallyldimethylammonium chloride (pDADMAC).

In certain embodiments of the invention, the substance may be released from the capsule or barrier when the polymeric membrane is dissociated.

In further embodiments of the invention, the substance may comprise one or more of the group consisting of cells, proteins, biocompatible particles, and chemical compounds.

In certain embodiments of the invention, the polymeric membrane is placed in a liquid medium in step (a). For example, the composition comprising the non-toxic polyanionic material is added to the liquid medium to provide a concentration of non-toxic polyanionic material of from 0.01 to 30 mg/mL (e.g. the concentration of the non-toxic polyanionic material is from 0.1 to 25 mg/mL, such as from 1 to 20 mg/mL).

In further embodiments of the invention, the cells may be kept in a cell releasing medium for from 1 minute to 16 hours (e.g. from 10 minutes to 1.5 hours, such as from 15 minutes to 75 minutes).

In a third aspect of the invention, there is disclosed a polyanionic sulfate composition for use in dissociating a polymeric membrane. In certain embodiments, the non-toxic polyanionic material is a polysaccharide sulfate, a poly (sodium styrene sulfonate) or a polyacrylic acid or a salt thereof, provided that the polysaccharide sulfate is not a glycosoaminoglycan.

In yet further embodiments of the invention, the non-toxic polyanionic material of the second and third aspects of the invention is as described in the first aspect of the invention.

Further aspects and embodiments of the current invention are described in the following clauses.

1. Use of a composition comprising a non-toxic polyanionic material or a salt thereof to dissociate a polymeric membrane.

2. The use of Clause 1, wherein the polymeric membrane is in the form of a capsule that encapsulates a substance or in the form of a barrier that blocks free movement of a substance.

3. The use of Clause 1 or 2, wherein the polymeric membrane comprises sodium cellulose sulfate and polydiallyldimethylammonium chloride (pDADMAC).

4. The use of any one of the preceding clauses, wherein the non-toxic polyanionic material is a polysaccharide sulfate, a poly(sodium styrene sulfonate) or a polyacrylic acid or a salt thereof.

5. The use of any one of Clauses 2 to 4, wherein the substance is selected from one or more of the group consisting of cells, proteins, biocompatible particles, and chemical compounds.

6. The use of Clause 5, wherein the substance is a plurality of cells.

7. The use of any one of the preceding clauses, wherein the polyanionic material or a salt thereof has a number average molecular weight of from 4,000 to 20,000 Daltons.

8. The use of Clause 7, wherein the polyanionic material or salt thereof has a number average molecular weight of from 4,500 to 15,000.

9. The use of Clause 8, wherein the polyanionic material or salt thereof has a number average molecular weight of from 5,000 to 10,000.

10. The use of Clause 9, wherein the polyanionic material or salt thereof has a number average molecular weight of 5,000.

11. The use of any one of the preceding clauses, wherein the polyanionic material or salt thereof is a polysaccharide sulfate.

12. The use of Clause 11, wherein each saccharide unit of the polysaccharide sulfate contains from 1 to 3 sulfate groups.

13. The use of Clause 12, wherein the polysaccharide sulfate or salt thereof is a carbohydrate sulfate or salt thereof, a glucosoaminoglycan sulfate or salt thereof or combinations thereof.

14. The use of Clause 13, wherein the carbohydrate sulfate is one or more of the group consisting of dextran sulfate and cellulose sulfate with a number average molecular weight of from 4,000 to 20,000 Daltons and salts thereof 15. The use of Clause 14, wherein the carbohydrate sulfate is dextran sulfate or a salt thereof.

16. The use of Clause 15, wherein the dextran sulfate is dextran sulfate sodium salt.

17. The use of Clause 13, wherein the glucosoaminoglycan sulfate is selected from the group consisting of heparin, heparan sulfate, chondroitin sulfate, dermatan sulfate and salts thereof.

18. The use of Clause 1, wherein the composition is an anti-clumping agent comprising dextran sulfate.

19. The use of any one of Clauses 4 to 18, wherein the composition contains the polysaccharide sulfate in a concentration of from 0.1 mg/mL to 100 mg/mL.

20. The use of Clause 19, wherein the composition contains the polysaccharide sulfate in a concentration of from 1 mg/mL to 20 mg/mL.

21. A method of dissociating a polymeric membrane, the method comprising the steps of:
   (a) providing a polymeric membrane; and
   (b) dissociating the polymeric membrane by adding a composition comprising a non-toxic polyanionic material to the polymeric membrane.

22. The method of Clause 21, wherein the polymeric membrane is in the form of a capsule that encapsulates a substance or in the form of a barrier that blocks free movement of a substance.

23. The method of Clause 21 or Clause 22, wherein the polymeric membrane comprises sodium cellulose sulfate and polydiallyldimethylammonium chloride (pDADMAC).

24. The method of Clause 22 or Clause 23, wherein the substance is released from the capsule or barrier when the polymeric membrane is dissociated.

25. The method of any one of Clauses 22 to Clause 24, wherein the substance comprises one or more of the group consisting of cells, proteins, biocompatible particles, and chemical compounds.

26. The method of any one of Clauses 21 to 25, wherein the polymeric membrane is placed in a liquid medium in step (a).

27. The method of Clause 26, wherein the composition comprising the non-toxic polyanionic material is added to the liquid medium to provide a concentration of non-toxic polyanionic material of from 0.01 to 30 mg/mL.

28. The method of Clauses 27, wherein the concentration of the non-toxic polyanionic material is from 0.1 to 25 mg/mL.

29. The method of any one of Clauses 21 to 28, wherein the concentration of the non-toxic polyanionic material is from 1 to 20 mg/mL.

30. The method of Clauses 25 to 29, wherein the cells are kept in a cell releasing medium for from 1 minute to 16 hours.

31. The method of Clause 30, wherein the cells are kept in the cell releasing medium for from 10 minutes to 1.5 hours.

32. The method of Clause 31, wherein the cells are kept in the cell releasing medium for from 15 minutes to 75 minutes.

33. The method of any one of Clauses 21 to 32, wherein the non-toxic polyanionic material is a polysaccharide sulfate, a poly(sodium styrene sulfonate) or a polyacrylic acid or a salt thereof.

34. The method of any one of Clauses 21 to 33, wherein the polyanionic material or a salt thereof has a number average molecular weight of from 4,000 to 20,000 Daltons.

35. The method of Clause 34, wherein the polyanionic material or salt thereof has a number average molecular weight of from 4,500 to 15,000.

36. The method of Clause 35, wherein the polyanionic material or salt thereof has a number average molecular weight of from 5,000 to 10,000.

37. The method of Clause 36, wherein the polyanionic material or salt thereof has a number average molecular weight of 5,000.

38. The method of any one of Clauses 21 to 37, wherein the polyanionic material or salt thereof is a polysaccharide sulfate.

39. The method of Clause 38, wherein each saccharide unit of the polysaccharide sulfate contains from 1 to 3 sulfate groups.

40. The method of any one of Clauses 33 to 39, wherein the polysaccharide sulfate or salt thereof is a carbohydrate sulfate or salt thereof, a glucosoaminoglycan sulfate or salt thereof or combinations thereof.

41. The method of Clause 40, wherein the carbohydrate sulfate is one or more of the group consisting of dextran sulfate and cellulose sulfate with a number average molecular weight of from 4,000 to 20,000 Daltons and salts thereof 42. The method of Clause 41, wherein the carbohydrate sulfate is dextran sulfate or a salt thereof.

43. The method of Clause 42, wherein the dextran sulfate is dextran sulfate sodium salt.

44. The method of Clause 40, wherein the glucosoaminoglycan sulfate is selected from the group consisting of heparin, heparan sulfate, chondroitin sulfate, dermatan sulfate and salts thereof.

45. A polyanionic sulfate composition for use in dissociating a polymeric membrane.

BRIEF DESCRIPTION OF FIGURES

Aspects and embodiments will be described with reference to the following figures, wherein.

DETAILED DESCRIPTION

Figure 1:
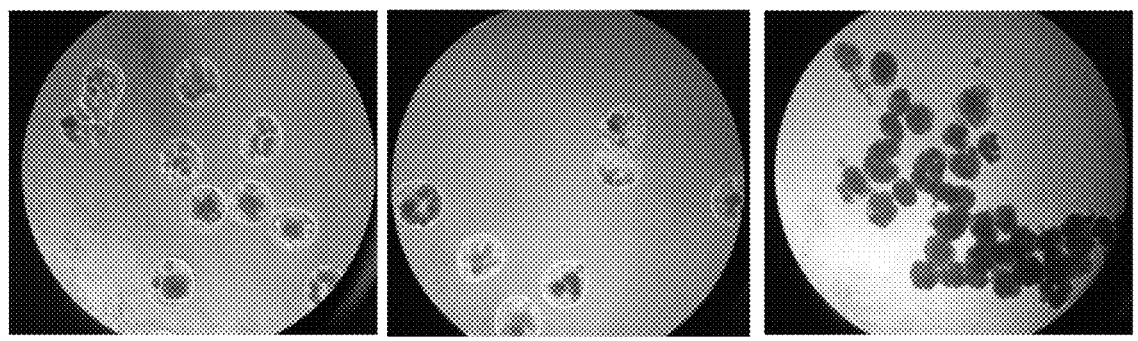
FIG. 1 is microscopic image (40× magnification) illustrating the effect of the dextran sulfate stock solution (10× dilution) on the capsules integrity over time. The left panel shows the capsules before the addition of dextran sulfate, the middle panels shows the capsules immediately after addition of dextran sulfate and the right panel shows the capsules 30 minutes after the addition of dextran sulfate.

Surprisingly, it has been found that a composition comprising a non-toxic polyanionic material or salt thereof can be used to dissociate a polymeric membrane.

The dissociating of the polymeric membrane may be performed using a method comprising the steps of:
(a) providing a polymeric membrane; and
(b) dissociating the polymeric membrane by adding a composition comprising a non-toxic polyanionic material to the polymeric membrane.

When used herein, the term "polymeric membrane" refers to a material comprising two or more polymers in the form of a complex. Suitable polymers to form such a complex may include one or more polysaccharides containing sulfate groups or polysaccharide derivatives containing sulfate groups in combination with one or more polymers containing quaternary ammonium groups.

Examples of polysaccharides containing sulfate groups or polysaccharide derivatives containing sulfate groups include, but are not limited to, cellulose sulfate, cellulose acetate sulfate, carboxymethylcellulose sulfate, dextran sulfate, starch sulfate or any combination thereof. When the "polymeric membrane" comprises polysaccharides containing sulfate groups or polysaccharide derivatives containing sulfate groups, the sulfate groups may be in the form of a salt. For example, the sulfate groups may be in the form of a sodium salt.

Examples of polymers containing quaternary ammonium groups may include, but are not limited to, polydimethyldiallylammonium or polyvinylbenzyl-trimethylammonium. The quaternary ammonium groups may be in the form of a salt. In particular the quaternary ammonium groups may be in the form of a chloride salt.

For example, the polymeric membrane comprises a sodium cellulose sulfate (SCS) and polydiallydimethylammonium chloride (pDADMAC), wherein the sodium cellulose sulfate and polydiallydimethylammonium chloride form a polymer complex. Without wishing to be bound by theory, such polymer complexes may be formed via the electrostatic interactions between the polysaccharide containing sulfate groups and the polymers containing quaternary ammonium groups. For example, the electrostatic interactions may occur between the negatively charged anionic sulfate group of sodium cellulose sulfate and the positively charged cationic group of the polydiallydimethylammonium chloride.

The polymeric membrane, as described herein, may be used to encapsulate one or more substances, or form a barrier to restrict the movement of one or more substances. When used herein the terms "encapsulate", "encapsulated" and "encapsulating" refer to the enclosing of a substance by a polymeric membrane. This may be done by forming a capsule (made from the polymeric membrane) around the substance. For example, a polymeric membrane comprising a sodium cellulose sulfate (SCS) and polydiallydimethylammonium chloride (pDADMAC) polymer complex may form a capsule around cells thus encapsulating the cells, within a SCS/pDADMAC capsule.

When discussed herein, the term "substance" refers to any material or matter capable of being encapsulated by the polymeric membrane. Moreover, where the polymeric membrane forms a barrier when in the form of a capsule, the term "substance" refers to any material or matter capable of being separated from another substance without passing through the barrier. Typical examples of a "substance" as used herein, may be selected from one or more of the group consisting of cells, proteins, biocompatible particles chemical compound or any combination thereof. In particular the substance may be cells. Examples of cells may include, but are not limited to, mammalian cells, insect cells, plant cells, bacterial cells, fungal cells, protozoan cells or any combination thereof. Furthermore, the cells may be living cells or dead cells.

When the polymeric membrane is used to encapsulate a substance (i.e. forming a capsule around the substance), the polymeric membrane is capable of blocking the encapsulated substance from passing through the membrane wall and into the non-encapsulated external environment. Moreover, when the polymeric membrane is used to form a barrier to block the movement of one or more substances, the polymeric membrane is capable of blocking the one or more substances from passing through the barrier.

When the polymeric membrane forms a capsule or a barrier, which is capable of blocking substances from passing through the capsule wall or barrier, it may also be capable of allowing the selective passage of water and other solvents, small chemical compounds and biomolecules such as cytokines, antibodies and insulin across the capsule wall or the barrier, due to the polymeric membrane comprising pores.

The pore size of the polymeric membrane may be from 20 to 300 nm (e.g. 20 to 250 nm, from 80 to 225 nm, from 100 to 200 nm, from 150 to 175 nm, from 80 to 100 nm or from 200 to 300 nm). Further examples of constituents which may pass through these pores, include but are not limited to, drugs, delivery vectors and therapeutic biomolecules. More particularly, therapeutic biomolecules include, but are not limited to, antibodies, cytokines and insulin.

When used herein, the term "polyanionic material" is a polymer whose repeating unit includes at least one anionic group. An anionic group is a chemically functional group that can dissociate at physiological pH and which renders the polymers negatively charged. Examples of anionic groups include, but are not limited to, carboxylates, sulfates, nitrates and phosphates. It will be appreciated that the polyanionic material must be different in some way to SCS as used in the SCS/pDADMAC system. For example, the molecular weight of the polyanionic material may be significantly less than the SCS as used in the SCS/pDADMAC system. For example, the molecular weight of SCS (or similar materials used in the polymeric membrane) may be at least 2× (e.g. at least 3×, 4×, 5×, 10×, 20×) greater than the molecular weight of the polyanionic material used disrupt said membrane.

The polyanionic material may be one or more inorganic polymers or salts thereof or, more particularly, one or more organic polymers or salts thereof. Examples of suitable organic polymers include, but are not limited to, polysaccharides, polypeptides, a poly(sodium styrene sulfonate) or a polyacrylic acid. The polysaccharides may include polysaccharide sulfates or salts thereof, wherein the repeating saccharide unit includes at least one sulfate group. Examples of polysaccharide sulfates may be selected from the group consisting of a glucosoaminoglycan sulfate or, more preferably, a dextran sulfate, or combinations thereof. Examples of glucosoaminoglycan sulfate may be selected from the group consisting of heparin, heparan sulfate, chondroitin sulfate, dermatan sulfate and salts thereof. In certain embodiments, the non-toxic polyanionic material may be a polysaccharide sulfate, a poly(sodium styrene sulfonate) or a polyacrylic acid or a salt thereof, provided that the polysaccharide sulfate is not a glycosoaminoglycan.

In certain examples, the polysaccharide sulfate may be dextran sulfate or a salt thereof or, more particularly, sodium dextran sulfate.

The average molecular weight of the polyanionic material or a salt thereof may be from 4,000 to 20,000. In particular, the average molecular weight of the polyanionic material (e.g. polysaccharide sulfate) or salt thereof may be from 4,500 to 15,000, 5,000 to 10,000, 6,000 to 9,000 or 5,000. It will be appreciated that the polysaccharides containing sulfate groups used to form the polymer membrane have a molecular weight that is at least 2× (e.g. at least 3×, 4×, 5×, 10×, 20×) greater than the molecular weight of the polyanionic material used disrupt said membrane.

When the polyanionic material is a polysaccharide sulfate (e.g. provided that the polysaccharide sulfate is not a glycosoaminoglycan) or salt thereof, each saccharide unit (i.e. repeating unit) of the polysaccharide sulfate may include 1 to 3 anionic groups. For example, when the polysaccharide sulfate is dextran sulfate, the dextran sulfate may contain 3 sulfate groups.

The polyanionic material may be a non-toxic material. That is, the material does not cause cells exposed to the polyanionic material to die upon prolonged exposure (e.g. 10 minutes to 24 hours) to a concentration of the polyanionic material capable of dissociating the polymeric membrane.

A composition comprising a polyanionic material may be used to dissociate a polymeric membrane. As discussed herein, the terms "dissociate", "dissociating", "dissociation" and "dissociated" may be used to describe the process of dissociating or breaking a polymeric membrane into smaller pieces (i.e. dissociates). The terms "dissociate", "dissociating", "dissociation" and "dissociated" may be used interchangeably with other terms, such as "fragment", "fragmentation", "dissolve", "dissolution", "disrupt" or "disruption" which should also be understood to describe the process of dissociating or breaking a polymeric membrane into smaller pieces.

When the polymeric membrane comprises a polymer complex, the dissociation of of the polymer membrane may be due to the disruption of the electrostatic interactions in the polymer complex by the polyanionic material. For example, where the polymeric membrane comprises a sodium cellulose sulfate and polydiallydimethylammonium chloride polymer complex, the electrostatic interactions between the negatively charged anionic sulfate group of the sodium cellulose sulfate and the positively charged cationic group of the polydiallydimethylammonium chloride may be disrupted by the competing polyanionic material.

When the polymeric membrane encapsulates one or more substances, dissociation of the polymeric membrane will lead to the release of the encapsulated substance into a medium surrounding the former capsule (i.e. the capsule's external environment). For example, where an encapsulated substance is a plurality of cells and the environment surrounding the capsules is a cell culture medium, the cells are released into the cell culture medium upon dissociation of the polymeric membrane.

Alternatively, when the polymeric membrane forms a barrier that restricts the movement of one or more substances, the dissociation of the polymeric membrane will remove the barrier and allow the one or more substances to move freely without restriction.

The composition comprising the polyanionic material or salt thereof may be a solution. For example, the composition may be an organic solution or, more particularly, an aqeuous solution. When the composition is a solution, said composition may further comprise a solvent, a physiological buffer solution, a cell culture medium or any combination thereof.

Examples of suitable solvents include, but are not limited to water, dimethylsulfoxide, glycerol, skimmed milk, salt solutions, sucrose solutions and trehalose solutions.

Examples of physiological buffer solutions include, but are not limited to, phosphate buffer saline (PBS), A Good's buffer, 2-amino-2-hydroxymethyl-propane-1,3-diol (TRIS) buffer, phosphate buffers, 1,4-piperazinediethanesulfonic acid (PIPES) buffer, 2-(N-morpholino)ethanesulfonic acid (MES) buffer, 2-[(2-amino-2-oxoethyl)-(carboxymethyl)amino]acetic acid (ADA) buffer, 2-(carbamoylmethylamino)ethanesulfonic acid (ACES) buffer, 3-morpholino-2-hydroxypropanesulfonic acid (MOPSO) buffer, 3-morpholinopropane-1-sulfonic acid (MOPS) buffer, 2-{[1,3-dihydroxy-2-(hydroxymethyl)-2-propanyl]amino}ethanesulfonic acid (TES) buffer, 3-(N,N-bis[2-hydroxyethyl] amino)-2-hydroxypropanesulfonic acid (DIPSO) buffer, 3-[[1,3-dihydroxy-2-(hydroxymethyl)propan-2-yl]amino]-2-hydroxypropane-1-sulfonic acid (TAPSO) buffer, 3,3'-(1,4-piperazinediyl)bis(2-hydroxy-1-propanesulfonic acid) (POPSO) buffer, 3-[4-(2-hydroxyethyl)piperazin-1-yl]propane-1-sulfonic acid (HEPPS) buffer, N-(2-hydroxy-1,1-bis(hydroxymethyl)ethyl) (Tricine) buffer, 2-(bis(2-hydroxyethyl)amino)acetic acid (Bicine) buffer and 3-[[1,3-dihydroxy-2-(hydroxymethyl)propan-2-yl]amino]propane-1-sulfonic acid (TAPS) buffer.

Examples of cell culture medium include, but are not limited to, Luria-Bertani (LB) broth medium, Dulbecco's modified Eagle's medium (DMEM), Roswell Park Memorial Institute medium (RPMI), MRS medium, fetal bovine serum (FBS), M199 medium, Ham's medium, F12 medium and Williams medium.

The composition may be a solution which contains the polysaccharide sulfate in a concentration of from 0.1 mg/mL to 100 mg/mL, more preferably, from 1 mg/mL to 20 mg/mL. For example, the composition may be an aqueous sodium dextran sulfate solution wherein the concentration of the sodium dextran sulfate is 10 mg/mL.

In addition, the composition comprising a polyanionic material or salt thereof may be an anti-clumping agent comprising one or more polysaccharide sulfates. For example, the anti-clumping agent may comprise dextran sulfate. When used herein, the term anti-clumping agent refers to a reagent that reduces cell clumping/aggregation.

As discussed herein, the dissociation of the polymeric membrane may include any suitable method that includes:
providing a polymeric membrane; and
dissociating the polymeric membrane by adding a composition comprising a non-toxic polyanionic material to the polymeric membrane.

In certain examples, the polymeric membrane may be placed in a "medium". As described herein a "medium", refers to any suitable liquid, gel or gas capable of storing the polymeric membrane without compromising the integrity or chemical structure of the polymeric membrane. The polymeric membrane may be stored in the medium before it is dissociated. Examples of media include, but are not limited to, cell culture media, physiological buffer solutions, solvents or any combination thereof. Typical cell culture media may include, but are not limited to, Luria-Bertani (LB) broth medium, Dulbecco's modified Eagle's medium (DMEM), Roswell Park Memorial Institute medium (RPMI), MRS medium, fetal bovine serum (FBS), M199 medium, Ham's medium, F12 medium and Williams medium. For example, the cell culture medium is standard Dulbecco's modified Eagle's medium (DMEM) supplemented with 10% fetal bovine serum (FBS).

When the medium is a liquid medium, the non-toxic polyanionic material may be added to the liquid medium to provide a concentration of the non-toxic polyanionic material in the liquid medium of from 0.01 to 30 mg/mL. In particular, the concentration of the non-toxic polyanionic material in the liquid medium may be from 0.1 to 25 mg/mL, 1 to 20 mg/mL or 5 to 10 mg/mL. For example, where the polyanionic material is sodium dextran sulfate and the medium is standard Dulbecco's modified Eagle's medium (DMEM) supplemented with 10% fetal bovine serum (FBS) the concentration of the sodium dextran sulfate in the standard Dulbecco's modified Eagle's medium (DMEM) supplemented with 10% fetal bovine serum (FBS) may be 20 mg/mL.

When the polymeric membrane is used to encapsulate cells, the polymeric membrane may be dissociated to release the cells into a medium by adding a composition comprising non-toxic polyanionic material. The releasing of the cells in to the medium provides a "cell releasing medium". Accordingly, as described herein, "cell releasing medium" refers to any medium comprising the polymeric membrane (dissociated or non-dissociated) and the non-toxic polyanionic material.

The cells may be kept in the cell releasing medium for from 1 minute to 24 hours (e.g. 16 hours), 10 minutes to 1.5 hours or from 15 minutes to 75 minutes.

Accordingly, the composition comprising the non-toxic polyanionic material may be capable of releasing encapsulated cells without causing any significant damage to the released cells. This is illustrated by the cell viability studies below. The released cells (i.e. non-encapsulated cells) may then be used for further downstream processing.

The current method of dissociating of the polymeric membrane may be used in, but not limited to, large scale pharmaceutical grade manufacturing, biomedical applications, neutraceutical applications, probiotics, cosmetic applications, agriculture and environmetal applications.

Experimental
Materials and Methods
Preparation of the Dextran Sulfate Stock Solution Dextran sulfate 5000 MW purchased from Sigma Aldrich (Cat. No. #31404) was added to ultrapure water to provide a dextran sulfate stock solution having a concentration of 100 mg/mL. The dextran sulfate solution was filtered through a 0.2 µm filter under aseptic conditions and kept as a sterile stock solution. As an alternative, Gibco Anticlumping Agent (ACA, Cat. No. #0010057AE) containing approximately 100 mg/mL of dextran sulfate was also used.

Cell Viability and Cell Culture Medium

Cell viability was assayed using Prestoblue™ from Lifetech (Cat. No. A-13262). The cells used during the experiments below are HEK293 cells and the medium used for cell culture was standard Dulbecco's modified Eagle's medium (DMEM) supplemented with 10% fetal bovine serum (FBS).

Capsule Dissociating Experiments

100 SCS/pDADMAC capsules, with or without encapsulated cells, were placed in 8 mL of DMEM supplemented with 10% FBS inside a 6-well multiwell dish. An aliquot of the dextran sulfate stock solution or ACA (at between 20 mg/mL and 1 mg/mL dilution) was added directly to the cell culture medium containing the SCS/pDADMAC capsules to provide a capsule dissociating solution. The capsule dissociating solution was incubated at 37° C. in a $CO_2$ incubator with constant horizontal agitation until the capsule material was dissociated, thus releasing the encapsulated cells into the cell culture medium. The time taken for dissociating of the capsule was tracked visually by microscopy and documented (see FIG. 1 and Table 1).

The capsule dissociating experiments were repeated several times using identical conditions. It was shown that the experiments could be consistently and reliably replicated.

Cell Viability Experiments

Cells released from 100 dissolved capsules (using the method described above for the capsule dissociating experiments) were pelleted and resuspended in cell culture media. One tenth of the suspension, equivalent to 10 capsules-worth of cells (approximately $1\times10^5$ HEK293 cells), were then used for the Prestoblue™ cell viability assay.

The suspended cells obtained using the method as described above, were placed in a 96-well microplate in cell culture media and supplemented with dextran sulfate stock solution or ACA to a working concentration between 1 and 20 mg/mL. The cells were incubated for 1 and 2 hours at 37° C. in a $CO_2$ incubator and then subsequently assayed for cell viability using Prestoblue®.

Results
Time-Dependent Capsule Dissociating Studies

Time-dependent studies of capsule dissociation were carried out. The capsule dissociation was performed using the methods described in the capsule dissociation experiments provided above. The results of the time-dependent studies are discussed below with reference to FIGS. 1 and 2 as well as Table 1.

The microscopic image (40× magnification) of FIG. 1 illustrates the effect of the dextran sulfate stock solution (10× dilution, 10 mg/mL) on the integrity of the capsules over time.

In FIG. 1, the left panel shows the capsules before the addition of dextran sulfate. The middle panel shows the capsules starting to crumple and the capsule membrane beginning to lose integrity immediately after the addition of the dextran sulfate stock solution. The right panel illustrates that 30 minutes after the addition of dextran sulfate stock solution the capsule has completely dissociated and clumps of cells remain. Over time the capsules were observed to dissociate into progressively smaller pieces.

Figure 2:
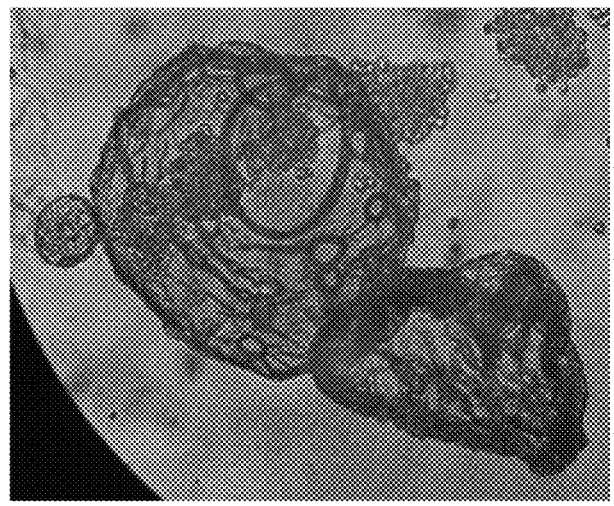
FIG. 2 is a microscopic image (150× magnification) illustrating a capsule dissociating.

FIG. 2 is a microscopic image (150× magnification) illustrating a capsule dissociating. The capsule was dissociated using a dextran sulfate stock solution at 4 mg/mL and is shown to crumple and lose its membrane integrity within 15 minutes of adding the dextran sulfate stock solution. Clusters of HEK293 cells can be seen released from the capsule into the external environment (upper-right corner of the image).

Table 1 illustrates the time taken for capsules to completely dissociate at different concentrations of dextran sulfate or ACA. Capsules were incubated with a dextran sulfate stock solution with varying concentrations (10, 5 and 1 mg/mL) and ACA solutions with varying dilutions (20×, 40× and 80× dilution, having dextran sulfate concentrations of 5, 2.5, 1.25 mg/mL respectively). The capsules were then observed by microscopy (40× magnification) every 15 minutes and complete dissociation of the capsules was judged to have occurred at the time when no capsule material could be visualised under microscopy (e.g. as shown in FIG. 1, right panel). Referring to Table 1, a tick is given for the complete dissociation of the capsules and a cross is given for anything less than complete dissociation of the capsules.

| Time of complete capsule dissociating (minutes) | dextran sulfate solution (10 mg/mL) | dextran sulfate solution (5 mg/mL) | Anti-clumping agent solution (20X dilution, 5 mg/mL) | Anti-clumping agent solution (40X dilution, 2.5 mg/mL) | Anti-clumping agent solution (80X dilution, 1.25 mg/mL) | dextran sulfate solution (1 mg/mL) |
|---|---|---|---|---|---|---|
| 0  | X | X | X | X | X | X |
| 15 | ✓ | X | X | X | X | X |
| 30 | ✓ | ✓ | ✓ | X | X | X |
| 45 | ✓ | ✓ | ✓ | ✓ | X | X |
| 60 | ✓ | ✓ | ✓ | ✓ | ✓ | X |
| 75 | ✓ | ✓ | ✓ | ✓ | ✓ | ✓ |

As seen from Table 1, there is a positive correlation between the dextran sulfate concentration and the time taken for the capsules to completely dissociate. At a concentration of between 1 and 10 mg/mL of dextran sulfate solution, full capsule dissociation can be obtained at between 15 and 75 minutes. The time taken for the ACA solution with a dilution of 20× to fully dissociate capsules corresponds to that of the dextran sulfate solution with a concentration of 5 mg/mL. This is consistent that the ACA solution has a dextran sulfate concentration of 100 mg/mL before dilution.

The extent of dissociation of the capsules is dependent on the quantity of dextran sulfate added to the capsules, whilst the rate of dissociation is influenced by the concentration of the dextran sulfate solution, temperature and agitation.

The cells released from the capsule during the time-dependent studies were recovered and can be used for further processing.

Cell Viability Assay

Cell viability assays were performed to investigate the effect of the dextran sulfate on the viability of the cells. The cell viability assay was performed using methods as described for the cell viability experiments above and the results can be seen illustrated in FIG. 3.

Figure 3:
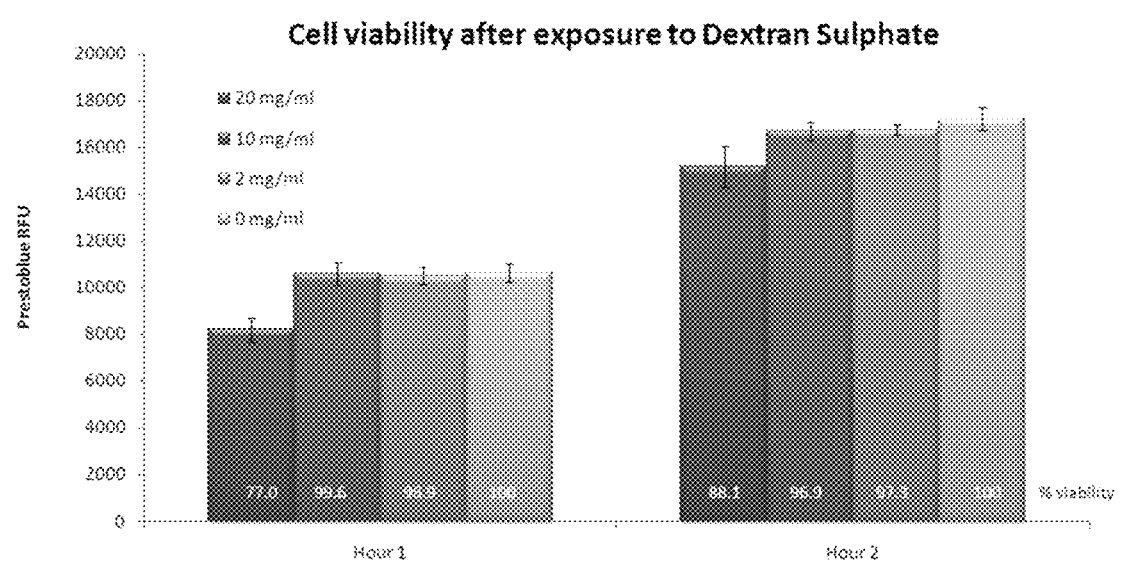
FIG. 3 illustrates HEK 293 cell viability observed (using Prestoblue™) over time whilst incubating with dextran sulfate solutions with varying concentrations (i.e. 0-20 mg/mL).

FIG. 3 illustrates the HEK 293 cell viability observed (using Prestoblue™) over time whilst incubating the cells with dextran sulfate solutions with varying concentrations (i.e. 0-20 mg/mL).

As shown by FIG. 3, even relatively high dextran sulfate solution concentrations have very little effect on the viability of HEK293 cells. No significant drop in cell viability was observed when incubating the cells for up to 2 hours with dextran sulfate solution at a concentration of 10 mg/mL. A slight drop is cell viability to 77% was observed at 20 mg/mL, however, between hour 1 and hour 2, the viability increased to 88.1%, suggesting that the cells can recover quickly.

Figure 4:
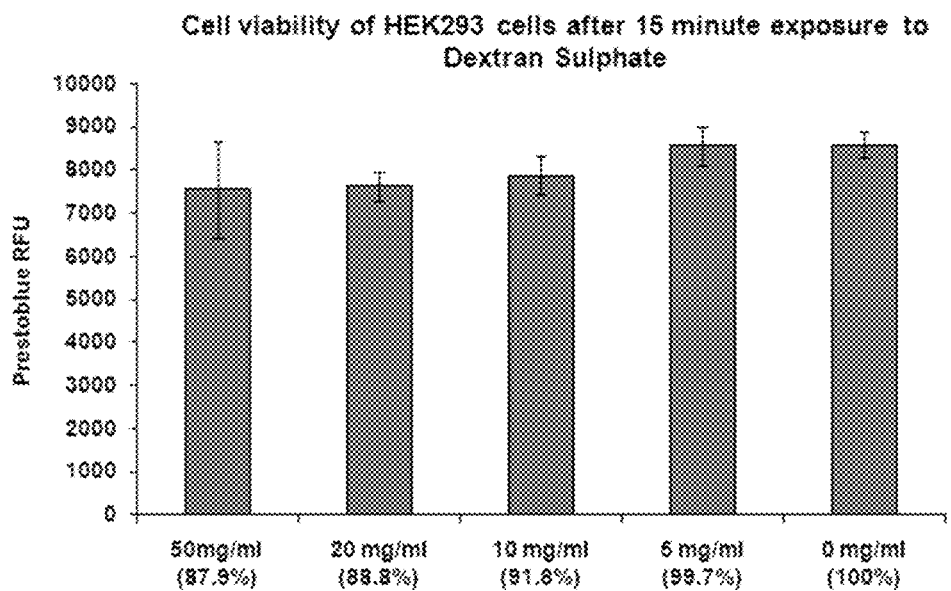
FIG. 4 illustrates HEK 293 cell viability observed (using Prestoblue™) at 15 minutes whilst incubating with dextran sulfate solutions with varying concentrations (i.e. 0-50 mg/mL).
Figure 5:
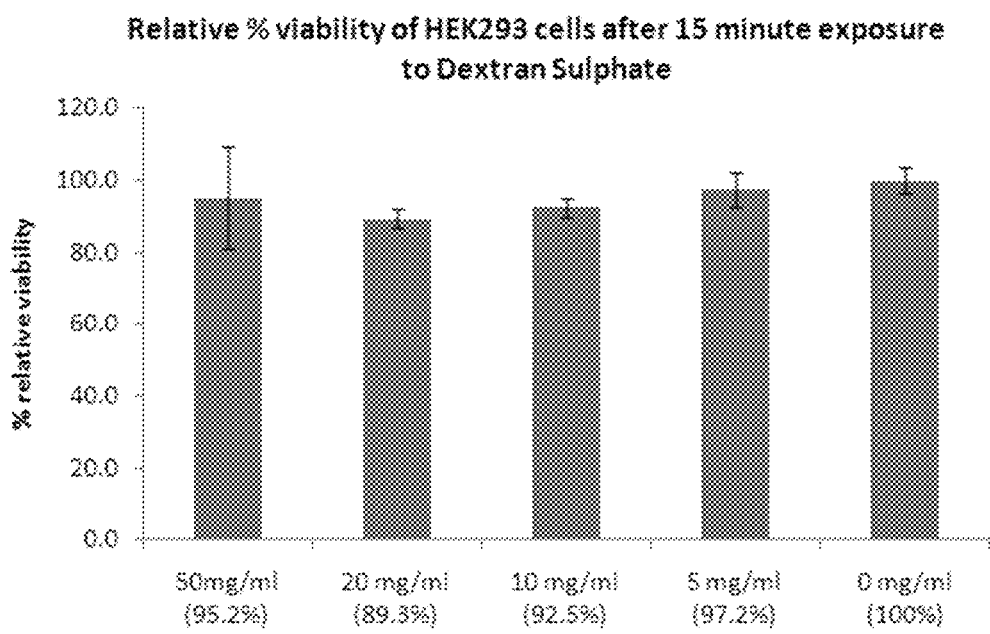
FIG. 5 illustrates relative (%) HEK 293 cell viability observed (using Prestoblue™) at 15 minutes whilst incubating with dextran sulfate solutions with varying concentrations (i.e. 0-50 mg/mL).

FIGS. 4 and 5 illustrates the HEK 293 cell viability observed (using Prestoblue™) at 15 minutes whilst incubating the cells with dextran sulfate solutions with varying concentrations (i.e. 0-50 mg/mL). As shown by FIGS. 4 and 5, even at higher dextran sulfate concentrations (50 mg/mL) the cell viability is not significantly reduced.

REFERENCES

1. Bioencapsulation of Living Cells for Diverse Medical Applications. E-Book. Editors: Brandtner E M, Dangerfield J A. Bentham Science Publishers; 2013. 184 p.
2. Lohr M, Bago Z T, Bergmeister H, Ceijna M, Freund M, Gelbmann W, et al. Cell therapy using microencapsulated 293 cells transfected with a gene construct expressing CYP2B1, an ifosfamide converting enzyme, instilled intra-arterially in patients with advanced-stage pancreatic carcinoma: a phase I/II study. J Mol Med. 1999; 77(4): 393-8.
3. Lohr M, Hoffmeyer A, Kroger J, Freund M, Hain J, Holle A, et al. Microencapsulated cell-mediated treatment of inoperable pancreatic carcinoma. Lancet. 2001; 357 (9268):1591-2.
4. Lohr M, Kroger J C, Hoffmeyer A, Freund M, Hain J, Holle A, et al. Safety, feasibility and clinical benefit of localized chemotherapy using microencapsulated cells for inoperable pancreatic carcinoma in a phase I/II trial. Cancer Therapy. 2003; 1:121-31.
5. Hauser O, Prieschl-Grassauer E, Salmons B. Encapsulated, genetically modified cells producing in vivo therapeutics. Current opinion in molecular therapeutics. 2004; 6(4):412-20. Epub 2004/10/08.
6. Schaffellner S, Stadlbauer V, Stiegler P, Hauser O, Halwachs G, Lackner C, et al. Porcine islet cells microencapsulated in sodium cellulose sulfate. Transplantation proceedings. 2005; 37(1):248-52. Epub 2005/04/06.
7. Stadlbauer V, Stiegler P B, Schaffellner S, Hauser O, Halwachs G, Iberer F, et al. Morphological and functional characterization of a pancreatic beta-cell line microencapsulated in sodium cellulose sulfate/poly(diallyldimethylammonium chloride). Xenotransplantation. 2006; 13(4):337-44. Epub 2006/06/14.
8. Pelegrin M, Marin M, Oates A, Noel D, Saller R, Salmons B, et al. Immunotherapy of a viral disease by in vivo production of therapeutic monoclonal antibodies. Human gene therapy. 2000; 11(10):1407-15. Epub 2000/07/26.
9. Salmons B, Hauser O, Gunzburg W H, Tabotta W. GMP production of an encapsulated cell therapy product: issues and considerations. BioProcessing. 2007; 6(2):37-44.
10. Dangerfield J A, Salmons B, Randolph C, Abastado J-P, Sinden J, Gunzburg W H, et al. The Diversity of Uses for Cellulose Sulfate Encapsulation. Chapter 3 in E-Book: Brandtner E M and Dangerfield, J. A., Eds. Bioencapsulation of Living Cells for Diverse Medical Applications. Bentham Science Publishers; 2013. p. 70-92.
11. Gunzburg W H, Salmons B. Stem cell therapies: on track but suffer setback. Current opinion in molecular therapeutics. 2009; 11(4):360-3. Epub 2009/08/04.

The invention claimed is:

1. A method of dissociating a polymeric membrane consisting of the steps of:
   (a) providing a polymeric membrane; and
   (b) dissociating the polymeric membrane by adding a composition comprising a non-toxic polyanionic material or a salt thereof to the polymeric membrane,
   wherein the non-toxic polyanionic material or a salt thereof is a polysaccharide sulfate or a salt thereof, provided that the polysaccharide sulfate is not a glycosoaminoglycan, wherein each saccharide unit of the polysaccharide sulfate contains from 1 to 3 sulfate groups.

2. The method of claim 1, wherein the polymeric membrane is placed in a liquid medium in step (a), wherein the composition comprising the non-toxic polyanionic material is added to the liquid medium to provide a concentration of non-toxic polyanionic material of from 0.01 to 30 mg/mL.

3. The method of claim 1, wherein the polymeric membrane is in the form of a capsule that encapsulates a plurality of cells, wherein the cells are kept in a cell releasing medium for from 1 minute to 16 hours.

4. The method of claim 1, wherein the non-toxic polyanionic material or a salt thereof has a number average molecular weight of from 4,000 to 20,000 Daltons.

5. The method of claim 1, wherein
   the polysaccharide sulfate is cellulose sulfate or dextran sulfate with a number average molecular weight of from 4,000 to 20,000 Daltons and salts thereof.

6. The method of claim 1, wherein the polysaccharide sulfate is cellulose sulfate or dextran sulfate or a salt thereof.

7. The method of claim 6, wherein the polysaccharide sulfate has a number average molecular weight of from 4,000 to 20,000 Daltons.

* * * * *